United States Patent [19]
Edlund et al.

[11] Patent Number: 5,645,626
[45] Date of Patent: Jul. 8, 1997

[54] COMPOSITE HYDROGEN SEPARATION ELEMENT AND MODULE

[75] Inventors: David J. Edlund, Redmond; David D. Newbold; Chester B. Frost, both of Bend, all of Oreg.

[73] Assignee: Bend Research, Inc., Bend, Oreg.

[21] Appl. No.: 583,969

[22] Filed: Jan. 11, 1996

Related U.S. Application Data

[63] Continuation-in-part of Ser. No. 359,917, Dec. 19, 1994, Pat. No. 5,498,278, which is a continuation-in-part of Ser. No. 148,999, Nov. 8, 1993, Pat. No. 5,393,325, which is a continuation-in-part of Ser. No. 986,692, Dec. 7, 1992, Pat. No. 5,259,870, which is a continuation-in-part of Ser. No. 566,092, Aug. 10, 1990, abandoned.

[51] Int. Cl.[6] .................................................. B01D 53/22
[52] U.S. Cl. .............................. 95/56; 96/7; 96/11; 55/524
[58] Field of Search .................... 55/524; 95/55, 95/56; 96/7, 11

[56] References Cited

U.S. PATENT DOCUMENTS

| | | | |
|---|---|---|---|
| 2,597,907 | 5/1952 | Steiner et al. | 96/7 |
| 3,336,730 | 8/1967 | McBride et al. | 95/56 |
| 3,344,586 | 10/1967 | Langley et al. | 96/7 |
| 3,350,846 | 11/1967 | Makrides et al. | 95/56 |
| 3,410,058 | 11/1968 | Oswin | 96/7 |
| 3,428,476 | 2/1969 | Langley et al. | 96/11 X |
| 3,447,288 | 6/1969 | Juda et al. | 96/11 |
| 3,469,372 | 9/1969 | Yamauchi et al. | 96/11 |
| 3,486,301 | 12/1969 | Bonnet | 96/7 |
| 3,499,265 | 3/1970 | Langley et al. | 96/7 |
| 3,534,531 | 10/1970 | Eguchi et al. | 96/7 |
| 3,782,077 | 1/1974 | Hollister et al. | 96/11 |
| 3,881,891 | 5/1975 | Goltsov et al. | 95/56 |
| 4,243,536 | 1/1981 | Prölss | 96/7 X |
| 4,589,891 | 5/1986 | Iniotakis et al. | 96/11 |
| 5,139,541 | 8/1992 | Edlund | 95/56 |
| 5,217,506 | 6/1993 | Edlund et al. | 95/56 |
| 5,500,122 | 3/1996 | Schwartz | 96/7 X |
| 5,520,807 | 5/1996 | Myrna et al. | 96/7 X |
| 5,536,405 | 7/1996 | Myrna et al. | 96/7 X |

FOREIGN PATENT DOCUMENTS

| | | | |
|---|---|---|---|
| 0724479 | 12/1965 | Canada | 95/55 |
| 2005494 | 9/1970 | Germany | 95/56 |
| 59-062326 | 4/1984 | Japan | 96/7 |
| 1-148325 | 6/1989 | Japan | 96/7 |
| 1-297121 | 11/1989 | Japan | 96/7 |
| 1-304027 | 12/1989 | Japan | 96/7 |
| 2-017918 | 1/1990 | Japan | 96/7 |
| 2-017919 | 1/1990 | Japan | 96/7 |
| 2-017920 | 1/1990 | Japan | 96/7 |
| 2-144117 | 6/1990 | Japan | 96/11 |
| 0969673 | 9/1964 | United Kingdom | 95/56 |
| 1195852 | 6/1970 | United Kingdom | 95/56 |
| 1286670 | 8/1972 | United Kingdom | 95/56 |

*Primary Examiner*—Robert Spitzer
*Attorney, Agent, or Firm*—Chernoff, Vilhauer, McClung & Stenzel

[57] ABSTRACT

There are disclosed improvements in multicomponent composite metal membranes useful for the separation of hydrogen, the improvements comprising the provision of at least one common-axis hole through all components of the composite membrane and the provision of a gas-tight seal around the periphery of the hole or holes through a coating metal layer of the membrane.

43 Claims, 9 Drawing Sheets

COMPOSITE HYDROGEN SEPARATION ELEMENT AND MODULE

This is a continuation-in-part of application Ser. No. 08/359,917 filed Dec. 19, 1994, now U.S. Pat. No. 5,498,278 which is a continuation-in-part of application Ser. No. 08/148,999 filed Nov. 8, 1993, now U.S. Pat. No. 539,325 which is a continuation-in-part of application Ser. No. 07/986,692 filed Dec. 7, 1992, now U.S. Pat. No. 5,259,870, which is a continuation-in-part of application Ser. No. 07/566,092, filed Aug. 10, 1990, now abandoned.

The government has rights in this invention pursuant to Grant Nos. ISI-8722212 awarded by the National Science Foundation and DE-FG03-91ER81228 and DE-FG03-91ER81229 awarded by the Department of Energy.

BACKGROUND OF THE INVENTION

Membranes and membrane modules for separation of hydrogen from other gases are known. See Zolandz et al. at pages 95–98 in *Membrane Handbook* (1992). In particular, useful membranes for hydrogen separations are of four types: polymeric, porous ceramic, self-supporting, nonporous metal, and nonporous metal supported on a porous rigid matrix such as metal or ceramic.

Polymeric membranes are commonly used in the form of extended flat sheets or small diameter hollow fibers. Flat sheet polymeric membranes are most often incorporated into spiral-wound modules. In this case, the membrane forms an envelope around a flexible polymeric or cloth net (the permeate spacer). The edges of the membrane are glued together to form a gas-tight seal that separates the feed gas, which flows over the outer surface of the membrane envelope, from the permeate gas, which is collected in the cavity created by the permeate spacer. The permeate spacer forms a continuous channel connecting to a permeate collection tube that allows the permeate hydrogen to flow through the permeate spacer and into the permeate collection tube.

Hollow fiber membranes are incorporated into hollow-fiber modules which are very similar in design to shell-and-tube heat exchangers. Polymeric adhesives and sealants such as epoxy resins are used to seal the tubular or hollow fiber membranes into the module shell to form a gas-tight barrier. This allows the gas to be fed to either the interior or exterior of the fibers, thereby preventing gas from flowing into the permeate stream except by permeation through the fiber wall. In cases where the feed gas is directed to the interior of the fibers the hydrogen permeate is collected on the "shell" side or outside of the tubes or fibers.

Polymeric membranes and membrane modules for hydrogen separations suffer from a lack of high selectivity toward hydrogen over other gases resulting in a relatively impure product gas, a lack of stability at operating temperatures above 250° C., and chemical incompatibility with many chemicals such as hydrocarbons that are present in the impure hydrogen feed stream. To overcome these limitations, highly selective and more robust materials must be used for the hydrogen separation membrane and for sealing the membrane into the membrane module.

Inorganic materials, notably nonporous and porous ceramics and nonporous or dense metals, are known to make robust hydrogen-selective diffusion membranes. Such inorganic membranes are suitable for use at temperatures above 250° C. and are not damaged by many chemicals, including hydrocarbons.

Nonporous inorganic oxides are known to be permeable to hydrogen in its ionic form. For example, U.S. Pat. No. 5,094,927 discloses materials that are permeable to hydrogen ions (referred to as "solid-state proton conductors") based on silicon oxide, oxides of Groups IVB, VB, VIB and VIII of the Periodic Table, and fluorides of Groups IIA and IIIB of the Periodic Table. Additionally, diffusion coefficients for hydrogen ions through the oxides of molybdenum and tungsten have been reported by Sermon et al. in 72 *JCS Faraday Trans. I* 730 (1976).

Such solid-state proton conductors have been used by placing them between the cathode and anode in fuel cells, resulting in a net transport of hydrogen between the cathode and anode. However, these solidstate proton conductors are generally brittle, exhibit relatively low permeability to hydrogen, and have not generally been reported for use as a hydrogen separation membrane. The one exception is a nonporous silicon oxide membrane that is reported to allow hydrogen permeation through the silicon oxide by an activated surface-transport mechanism along grain boundaries. See Gavalas et al., 44 *Chem. Eng. Sci.* 1829 (1989). Although this dense silicon oxide membrane exhibits very high selectivities for hydrogen relative to nitrogen, it is also brittle and susceptible to reaction with steam at elevated temperatures, further limiting its utility.

Exemplary materials that have been investigated for use as porous inorganic molecular hydrogen-permeable membranes include aluminum oxide, silicon oxide, titanium oxide, magnesium oxide, chromium oxide, tin oxide, and various zeolites. See, for example, Hsieh, 33 *Catai. Rev. Sci. Eng.* 1 (1991). While such membranes exhibit very high hydrogen permeability, they also suffer from very low hydrogen selectivity due to their relatively large mean pore diameter and, as with the nonporous hydrogen-permeable ceramics discussed above, porous ceramics are also very brittle by nature and so are susceptible to failure due to cracking.

Porous ceramics, typically alpha- or gamma-aluminum oxide in the form of tubes, separate hydrogen from other gases based on differential gas phase diffusion rates through the pores of the ceramic. Such ceramic membranes are typically incorporated into a shell-and-tube module. A seal between the ceramic tube and the module shell, to prevent the feed gas from flowing directly into the permeate stream, is made by one of two methods: (1) polymeric o-rings are used to make the seal outside of any heated zone of the membrane module; or (2) graphite string or cord is used with metal compression fittings to make the seals within the heated zone of the membrane module. The use of polymeric sealing materials requires that the ends of the membrane module be kept cool, which is difficult when large volumes of gas are flowing through the module. Because these porous ceramic membranes have relatively low selectivity for hydrogen over other gases, the integrity of the seals is often difficult, if not impossible, to assess.

To overcome the inherently low selectivity of porous ceramic membranes, palladium- or palladium-alloy-coated ceramic membranes have been disclosed. See Hsieh, "Inorganic Membrane Reactors," 33 *Catal. Rev. Sci. Eng.* 1 (1991). Since nonporous or dense layers of hydrogen-permeable metals such as platinum, palladium, nickel and certain alloys thereof are permeable only to hydrogen, the selectivity for hydrogen over other gases is very high, which is a desirable characteristic of membrane-based separations. Such metal-coated ceramic membranes are typically incorporated into shell-and-tube modules using graphite gaskets within a compression fitting to seal the membrane tube to the module, thereby to prevent gas flow from the feed stream directly to the permeate stream. However, the large differences between the coefficient of thermal expansion of the ceramic tube and of the metal compression fitting, combined with the brittleness of the ceramic tube, results in a high frequency of leaks between the feed stream and the permeate stream at the gasket. See J. P. Collins, "Preparation and Characterization of a Composite Palladium-Ceramic Membrane,"32 *Ind. Eng. Chem. Res.* 3006 (1993). Another drawback of ceramic-supported thin metal foil membranes is that the metal foil is subject to macroscopic ruptures should the ceramic crack due to uneven loading or to thermal or mechanical shock.

Nonporous metal membranes that are selectively permeable to hydrogen are also known. See, for example, U.S. Pat. Nos. 4,388,479 and 3,393,098, both of which disclose Group VIIB and VIII alloy membranes such as palladium alloy catalytic membranes. Such metal membranes are superior to polymeric membranes and to inorganic (non-metal) membranes in that they have essentially complete selectivity for hydrogen over other gases, can be operated at temperatures up to about 1000° C., and are chemically resistant to gases in the feed stream. However, the prohibitively high cost of palladium has led to efforts to fabricate composite hydrogen-permeable metal membranes by coating certain less expensive transition metal alloy base metals with palladium or palladium alloys. See, for example, U.S. Pat. Nos. 4,468,235 and 3,350,846. The palladium or palladium-alloy coating on such base metals employs only a relatively small amount of palladium, imparting chemical resistance to the base metal and in some cases increasing the rate of adsorption of hydrogen onto the metal membrane surface.

U.S. Pat. No. 2,958,391 describes a metal membrane module consisting of a palladium or palladium alloy supported directly on a porous base metal comprising a sintered-metal matrix. The sintered-metal matrix may be in the shape of a flat plate or an elongated cylinder. Hydrogen permeates from the external surfaces of the palladium or palladium alloy membrane into the porous sintered-metal matrix, is conducted through its pore structure, and is collected.

In addition to porous ceramic and sintered-metal supports for hydrogen-permeable metal membranes, U.S. Pat. Nos. 3,477,288 and 4,699,637 disclose the use of a metal mesh or gauze to support the thin metal membrane. Means to fabricate membrane modules are not taught in these patents. However, Canadian Patent No. 1,238,866 describes the use of a silver-based solder to seal to the module the edges of a flat-sheet palladium alloy membrane supported on a metal mesh or gauze, porous sintered metal, or perforated metal.

However, such coated or supported metal membranes have an inherent shortcoming in that, under the elevated temperature conditions of use, the coating metal tends to diffuse into the base metal or porous metal support, thereby destroying both the hydrogen permeability and the chemical resistance available from such composite metal membranes. U.S. Pat. No. 4,496,373 discloses a nonporous hydrogen-permeable composite metal membrane that addresses this intermetallic diffusion problem for a base metal alloy of a specific composition coated with a palladium alloy of specific composition. However, the composition of the palladium alloy coating and the base metal alloy are narrowly defined so as to favor partitioning of the palladium into the coating alloy as opposed to the base metal alloy. Consequently, this approach is not general in nature, requires strict control over alloy composition, and allows for little variation in selection of metals for membrane fabrication.

A general approach to preventing intermetallic diffusion in composite metal membranes, disclosed in commonly owned U.S. Pat. Nos. 5,259,870 and 5,395,325, is to utilize a chemically and thermally stable intermediate layer between a coating metal layer and a dense hydrogen-permeable base metal. The coating metal layer comprises a dense (i.e., nonporous), hydrogen-permeable metal including palladium and palladium alloys. The base metal layer is also a dense, hydrogen-permeable metal and is selected from the metals found in Groups 3 through 5 of the Periodic Table and their hydrogen-permeable alloys. The intermediate layer (also called the intermetallic diffusion barrier) includes chemically and thermally stable oxides (e.g., aluminum oxide and silicon oxide) and serves to prevent direct contact between the coating metal layer and the base metal layer.

Japanese Laid-Open Application Nos. 346,824/92 and 76,738/93 both disclose a hydrogen gas separation membrane comprising a thin membrane of palladium, a porous metal support and a ceramic or metal oxide barrier layer between the palladium and the support. However, the barrier layer is inherently rigid and brittle.

PCT application No. 90/09231 discloses a hydrogen separation membrane comprising an inorganic support having interstices, the interstices of the support being bridged by a composite layer of partially sintered non-metallic particles and a hydrogen-permeable metal such as palladium, the bridging taking place in such a fashion as to render the composite layer coplanar with the support.

In all of these approaches to using an oxide layer to limit or prevent intermetallic diffusion in a composite metal membrane, the oxide layer is inherently brittle. Thus, membranes made according to these teachings are subject to failure due to formation of pinholes, cracks, and/or tears in the coating metal layer as a result of fracture of the brittle oxide layer directly beneath the coating metal layer.

The use of a chemically reactive intermediate oxide layer in hydrogen-permeable metal membranes is also known. In contrast to the chemically and thermally stable intermediate layers described above, such a reactive oxide layer facilitates, rather than prevents, intermetallic diffusion. For example, Russian Patent No. 1,058,587 discloses a method for manufacturing membrane elements for diffusion-based hydrogen separators by diffusion-welding palladium or palladium-alloy membranes to an undefined metal substrate. Specifically, the '587 patent discloses first saturating a hydrogen-permeable coating metal at elevated temperature, then cooling the so-hydrogen-loaded coating metal, then applying a "reactive gasket" of ultrafinely divided powders of metallic oxides over the area between a base metal and the coating metal where the base and coating metals are to be welded together, then subjecting the composite to high pressure (2000–2500 psi) and high temperature (650°–700° C.) to achieve a "diffusion weld" between the coating metal and the base support metal. The diffusion weld results from the complete reduction of the metal oxides "reactive gasket" intermediate layer to pure metal(s) by hydrogen desorbed from the hydrogen-loaded coating metal. It is unclear whether (1) the palladium or palladiumalloy membrane is attached only to the edges of the metal substrate via the diffusion-bonded weld, or (2) the palladium or palladium-alloy membrane completely covers the surface of the metal substrate and the diffusionbonded weld. In the first case, the welded portion of the membrane need not be hydrogen-permeable, as hydrogen is required only to permeate the unwelded portion of the palladium or palladium-alloy membrane and the hydrogen-permeable portion of the membrane is not a composite metal membrane at all, but rather is simply a palladium or palladium-alloy membrane. The drawback of such an approach is that the palladium or palladium-alloy membrane must be sufficiently thick to be self-supporting and the membrane is therefore unacceptably expensive. In the second case, the resulting composite membrane would include an intermediate layer which, after fabrication, is a metal or metal alloy, with attendant reduction in the overall hydrogen permeability of the membrane.

Despite the fact that hydrogen-permeable metal membranes were first commercialized nearly three decades ago, practical and affordable metal membrane modules are still lacking. Known module designs suffer from (1) high cost due to complex configurations and permanent assembly methods that make repairs difficult and expensive, (2) reduced membrane permeability due to interdiffusion of metallic constituents from the metal support matrix or from the module itself, and (3) physical damage of the membrane due to damage to the coating metal layer arising from dimensional changes in the membrane under the conditions of use, the damage ultimately leading to rupture. The present invention overcomes these and other shortcomings of the prior art.

SUMMARY OF THE INVENTION

The present invention comprises a composite hydrogen-permeable inorganic membrane and a module incorporating the membrane, both of which are capable of accommodating dimensional changes in the coating metal layer that occur in use, which prevents damage to both the coating metal and intermediate layers. The membrane comprises three elements: (1) a chemically and thermally stable porous intermediate layer between (2) a hydrogen-permeable coating metal layer and (3) a rigid support matrix. All three elements have at least one common axis hole therethrough.

The rigid support matrix lends structural strength to the composite metal membrane and so must be chosen with this in mind. Also, hydrogen must pass through the support matrix relatively unimpeded. A wide range of materials may be used as the support matrix, including porous, mesh, perforated, and slotted metals; and ceramics.

When the support matrix is a metal or metal alloy the provision of a flexible porous non-sintered intermediate layer (1) prevents intermetallic diffusion between the support matrix and the coating metal layer; (2) accommodates dimensional changes of the coating metal layer by expanding and contracting; and (3) establishes a conduit or pathway for permeate hydrogen to flow to any permeable portions of the support matrix.

When the coating metal layer is textured, the intermediate layer may be rigid. The provision of a textured coating metal layer allows accommodation of the natural expansion and contraction of that layer during use in such a manner as to prevent the formation of pinholes, cracks, tears and the like that would otherwise lead to mechanical failure of the coating metal layer. Texturing of the coating metal layer may be accomplished prior to or during the course of fabrication of the composite membrane module; in the latter case, foe example, the pattern of a textured intermediate layer may be embossed upon the coating metal layer by the application of pressure to the composite membrane.

The membrane module of the present invention comprises a housing fitted with at least one hydrogen separation membrane, at least one feed inlet port, at least one raffinate discharge port, and at least one permeate outlet port. Feed gas enters the module through the feed port and flows over the exterior surfaces of the membrane(s), eventually leaving the module as a hydrogen-depleted raffinate stream. The hydrogen separation membrane is a composite, comprising a coating metal layer, an intermediate layer, and a support matrix. The composite membrane has at least one hole along an axis that is substantially perpendicular to the membrane surfaces. Such an axial hole projects through all three components of the membrane along an axis that is essentially common to all three components and intersects the network of voids in the support matrix, thereby providing a conduit for permeate hydrogen from the support matrix to flow out of the membrane module, exiting the module through the permeate discharge port.

If more than one separation membrane is incorporated into the module, it is preferred to arrange the membranes in pairs, each pair comprising five components: a planar support matrix between a pair of intermediate layers, with a coating layer on the outer surface of each intermediate layer; the support matrix, intermediate layers and coating layers being of substantially the same construction as those components in the composite hydrogen separation membrane. At least one common-axis axial hole penetrates all five components of each membrane separator. A gas-tight gasket surrounding the common-axis hole is placed between successive separation membranes and separators within the module to prevent contamination of the permeate hydrogen by the feed gas flowing over the outer membrane surfaces.

DETAILED DESCRIPTION OF PREFERRED EMBODIMENTS

Figure 1A:
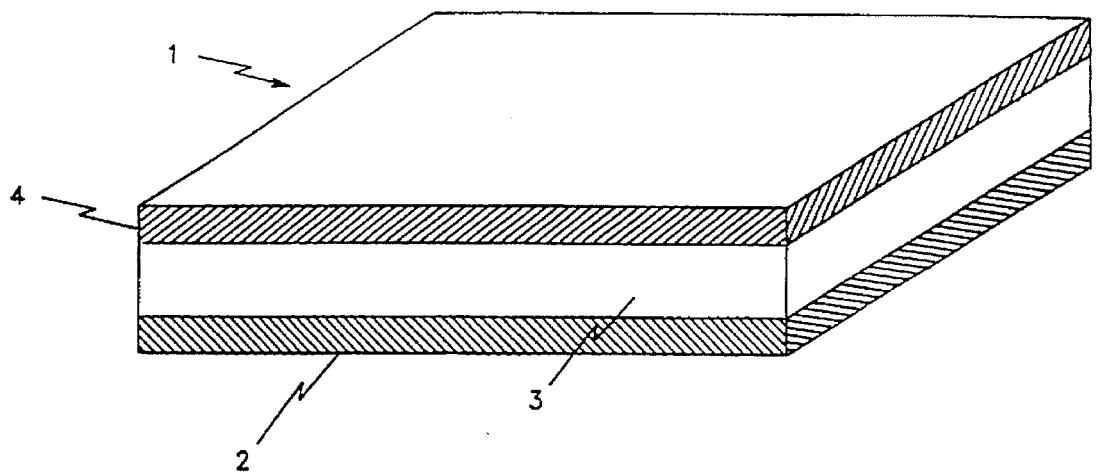
FIGS. 1a and 1b are schematic cross-sectional views of an exemplary composite hydrogen separation membrane of the present invention.

The overall composite membrane is selectively permeable to hydrogen gas and may be used in conventional fashion to separate hydrogen from other gases such as nitrogen, carbon monoxide, carbon dioxide, hydrogen sulfide, steam, ammonia or hydrocarbons such as methane, ethane, propane or olefins, all by conventional methods. Such methods involve the steps of (1) contacting a feed gas containing hydrogen and other gases at temperatures generally exceeding 200° C. and at a hydrogen partial pressure on the feed side of the membrane that is elevated relative to the hydrogen partial pressure on the permeate side of the membrane; (2) allowing the selective permeation of hydrogen through the composite membrane; and (3) collecting the permeated hydrogen. Since the membrane is selectively permeable to hydrogen even at temperatures of less than 200° C., such as at ambient temperatures (0° to 50° C.), the membrane has utility for separating hydrogen even at these lower temperatures, subject only to economic limitations, since the hydrogen permeability of the membrane is reduced at lower temperatures. Also, the permeate hydrogen need not be collected, but may be oxidized to form water or removed from the permeate side of the membrane with a sweep stream. The composite membrane is also useful in hydrogen separation methods such as are disclosed in U.S. Pat. No. 5,217,506. The hydrogen selectivity of the composite membrane is outstanding, exhibiting a selectivity of $\geq 100$ with a flux of 0.001 $m^3/m^2 \cdot hr$ at 400° C. and 100 psig hydrogen feed side pressure with the partial pressure of hydrogen on the permeate side at ambient pressure.

The composite membrane of the present invention is particularly stable under conditions of elevated temperature. Specifically, when exposed to a 100 psig hydrogen feed stream of $\geq 99.95\%$ purity at $\geq 400°$ C., with ambient pressure on the permeate side, the composite membrane retains $\geq 20\%$ of its initial flux over a continuous period of up to 250 days at 400° C. and up to 60 days at 600° C. This stability is directly attributable to the presence of the intermediate layer.

The support matrix is preferably ceramic or metal or carbon and serves two functions. First, it provides mechanical support to the thin metal membrane and the flexible intermediate layer so that the module can be operated with a large transmembrane pressure such as 10–600 psig difference between the feed and permeate pressures. Second, the matrix must allow hydrogen to pass relatively unimpeded through the multilayer composite membrane. As mentioned previously, the support matrix is preferably a material that has passages or voids through which hydrogen can pass, thus providing continuous channels that serve to collect the permeate hydrogen. The channels of the support matrix are sufficiently large to have acceptably low pressure drop as the permeate hydrogen flows through the support matrix to the axial hole and then to a collection tube or channel.

The rigid support matrix of the composite membrane provides mechanical support to the membrane and, as such, is selected primarily for its mechanical properties. The support matrix is preferably a perforated metal sheet, a slotted metal sheet, a porous sintered-metal sheet, or a metal mesh. The support matrix may also be dense and continuous (i.e., nonporous and without holes or perforations through the metal); in this configuration, a pathway must be provided for hydrogen permeating the coating metal to flow through the intermediate layer roughly parallel to the coating metal surface to the axial hole and through the membrane.

The chemical nature of the support matrix is of little significance so long as it does not react with either hydrogen or with the intermediate layer to cause a substantial decrease in the hydrogen flux through the composite membrane or to substantially weaken the composite membrane. For instance, the support should not comprise a metal or alloy that is severely embrittled in the presence of hydrogen under operating conditions. However, the support may be permeable to hydrogen in the sense that hydrogen dissolves and diffuses through it. Stainless steel, due to its strength, availability, and low cost, is a preferred material for use as the support. In the practice of the present invention, the thickness of the support is largely unimportant as long as the conditions are met that the support not impede hydrogen permeation and it provides mechanical or structural support to the composite membrane.

The coating metal is preferably at least one hydrogen-permeable metal that may be a transition metal or alloy or composite thereof. It should be chemically and physically stable at temperatures of at least 200° C., and is preferably selected from the transition metals of Groups VIIB and VIIIB of the Periodic Table, most preferably Fe, Mn, Ni, Pd, Pt, Ru, and hydrogen-permeable alloys containing $\geq 20$ wt % of said metals. For example, an alloy comprising 10–50 atom % silver, the remainder comprising palladium, is particularly preferred for applications wherein the feed contains <10 ppmv sulfur, such as in the form of $H_2S$, COS, mercaptans and thiols. When the feed contains $\geq 10$ ppmv sulfur, an alloy comprising 50–55 atom % Cu, the remainder comprising Pd is especially preferred for the coating metal; good resistance to sulfur attack has been observed with the use of such a coating metal at an operating temperature from about 500° C. to about 800° C. Another especially preferred alloy comprises 40–65 atom % copper, the remainder comprising palladium. The coating metal layer is dense and continuous in the sense that it is not porous and does not contain holes, cracks, or other breaks that span the thickness of the metal layer, and is preferably from 0.1 to 75 µm in thickness.

The coating metal layer of metal membranes often experiences dimensional changes due to changes in operating conditions such as temperature, hydrogen partial pressure, and transmembrane pressure. For instance, a coating metal layer comprising an alloy of palladium with 25% silver expands about 3% when exposed to hydrogen under typical hydrogen separation conditions. To avoid damage to either the coating metal or intermediate layers and consequent failure of the composite membrane, it is important to accommodate such expansion of the coating metal layer in a controlled manner. As previously mentioned, it has been discovered that this expansion may be accommodated by (1) use of a flexible material for the intermediate layer; or by (2) use of a textured coating metal; or by a combination of both (1) and (2).

When accommodation of dimensional changes is attributable in whole or in part to the intermediate layer, that layer may generally be described as comprising porous, non-sintered materials, compounds, and complexes other than pure metals and metal alloys; it is preferably a material selected from thermally stable woven and non-woven fabrics, papers, and felts.

The intermediate layer may be from 1 to 500 µm in thickness and forms a continuous layer between the support matrix and the coating metal, and further serves to prevent contact between the base metal and the coating metal. The intermediate layer is porous or microporous, which allows hydrogen to flow both parallel to the plane of the layer and perpendicular to and through the plane of the layer, both flow modes contributing to low resistance to the hydrogen flow.

The intermediate layer is chemically stable in the sense that under the conditions of use (at temperatures in the 200° to 1000° C. range), it does not react with the support matrix, the coating metal, or hydrogen to produce a layer comprising a compound, complex, or alloy that is substantially impermeable to hydrogen or to substantially reduce the tensile strength of the support matrix so as to compromise its utility. The intermediate layer is also thermally stable in the sense that it does not melt, sinter, or fuse at the elevated temperatures of use (200° C. to 1000° C.) to an extent that reduces the porosity of the layer, thereby to substantially increase its resistance to the flow of hydrogen.

Furthermore, when a flexible intermediate layer is used to accommodate expansion in the coating metal layer, it should be flexible in the sense that it is not brittle and lacks rigidity (i.e., it can be bent repeatedly to 180° with a radius of curvature of about 5 mm without cracking). Such flexibility is preferably retained following operation at elevated temperatures. The mechanical properties of the flexible intermediate layer allow it to be deformed, as by expanding or contracting ($\Delta L/L \geqq 0.005$ where L is the length of the layer of material) without cracking or breaking. Such deformability may be achieved in a variety of ways. For example, fibers comprising the intermediate layer may be slidable with respect to adjacent fibers. Alternatively, fibers of the intermediate layer may be corrugated so as to allow expansion and contraction without rupture, fracture, or other mechanical failure.

The chemical composition of the intermediate layer may be described as ceramic and glass fibers; the oxides of aluminum, silicon, boron, calcium, magnesium, and mixtures thereof; nitrides and carbides of boron; nitrides, carbides, and borides of silicon and aluminum; oxides, sulfides, carbides, borides, and nitrides of all of the Lanthanide metals, scandium, yttrium, molybdenum, tungsten, and all of the Group IVB and VB metals; silicides of all of the Group IVB and VB metals, and of scandium, yttrium, and all of the Lanthanide metals; zeolites; carbon; and chemically and thermally stable mixtures containing $\geqq 50\%$ of such materials, compounds, and complexes. Preferred exemplary woven fabrics include fiberglass cloth, 3M's NEXTEL™, zirconia cloth types ZYW15 and ZYW30A (Zircar Products, Inc. of Florida, New York), and SILTEMP™ 84CH (Ametek, Inc. of Wilmington, Del.). Examples of preferred non-woven fabrics, papers, and felts include APA-1, APA-2, APA-3, AS-1260, Type ZYF, Type D, and Type 99 (all from Zircar Products).

An important characteristic of the flexible intermediate layer is that it comprises a non-sintered material. The term "non-sintered" means that the material comprising the intermediate layer does not become a substantially isotropic, sintered composition either prior to or during fabrication of the composite metal membrane or after 1000 hours under operating conditions. The term "sintering" is common to the art of fabricating ceramic materials from powders and, in general, refers to a multi-step thermal densification process. See *Kirk-Othmer Encyclopedia of Chemical Technology*, page 265 (1979). In the first step of sintering on a micro scale, diffusion of material toward the points of contact among adjacent particles occurs, which initiates fusion between the particles. As high temperature (typically >1000° C.) is applied, fusion and coalescence takes place. The application of pressure to the mass to be sintered facilitates the process. As heating continues, particularly under applied pressure, the ceramic particles continue to fuse together and coalesce, eventually leading to fusion of the particles into a single ceramic piece, and ultimately eliminating all porosity from the ceramic mass. Sintering results in a material that is isotropic with respect to its mechanical properties. Sintering is generally undesirable for the intermediate layer of the composite membrane of the present invention because porosity is desirable and because sintering tends to yield an inherently brittle and inflexible structure which limits stretching (neighboring particles or fibers become fused and therefore can no longer slide past each other).

When the support matrix is a rigid metal, the intermediate layer serves to prevent contact between the coating metal layer and the metal support, thereby preventing interdiffusion of the metals which, in many cases, can lead to reductions as great as 95% in hydrogen flux through the membrane (see U.S. Pat. No. 5,259,870). The intermediate layer also serves to bridge gaps and smooth irregularities in the surface of the supporting metal matrix. In modules utilizing a rigid ceramic support matrix, the intermediate layer serves to bridge gaps in the surface, to smooth surface irregularities, and to protect the thin coating metal layer from damage should the rigid ceramic support matrix crack during use.

As previously mentioned, unwanted expansion of the coating metal layer may be accommodated by use of a textured coating metal. As used with respect to this invention, "textured" means closely spaced undulations, corrugations, ridges, ribs, dimples, lumps, or bumps in one or two dimensions. The coating metal layer is in contact with the intermediate layer, the latter being flexible or non-flexible. A woven or otherwise textured intermediate layer (flexible or non-flexible) may be utilized to impart texturing to the coating metal layer during the operation of the composite membrane. For instance, an intermediate layer such as woven glass, ceramic, or carbon cloth may serve as a template to impart substantially the same texturing to the coating metal layer in situ when the composite membrane is heated (to >200° C., preferably >500° C.) and simultaneously compressed ($\geqq 200$ psig). The topography of the textured coating metal layer is preferably such that the spacing between the undulations, bumps, dimples, corrugations, ridges, etc. is from about 0.5 to about 100 times the coating layer thickness. The mean height of such texturing is preferably such as to allow displacement of the coating metal layer out of its primary plane. It has been observed that a mean height of at least 10% of the spacing between undulations, etc. is satisfactory.

The intermediate layer need not be flexible to accommodate the dimensional changes of the textured coating layer. It has been observed that a composite membrane having a textured coating metal layer that is cycled between expansion and contraction appears to develop dimensional changes through a multitude of small displacements of the coating metal layer at or near each undulation, etc. By way of contrast, it has been observed that a composite membrane having a non-textured coating metal layer that is similarly cycled between expansion and contraction develops dimensional changes that tend to accumulate in either a single or a few large "wrinkle" displacements of the coating metal layer, accompanied by the simultaneous appearance of holes at or near the "wrinkles," with attendant failure of the membrane.

Use of both a textured coating metal layer and a flexible intermediate layer has been found to be a particularly preferred embodiment of the present invention.

Referring to FIG. 1a, there is shown a preferred exemplary embodiment of a three-layer composite membrane 1 comprising a support matrix 2, a flexible, non-sintered, porous or microporous intermediate layer 3, and a coating metal layer 4 (which comprises one or more layers).

The composite metal membrane may be fabricated by placing the coating metal layer (in the form of a thin foil that is textured or smooth), the flexible intermediate layer, and the base metal layer in contact with each other and sealed into a test cell or module by means of a gasket placed between the cell or module and the coating metal layer, or by brazing or welding the assembled composite in place. The three layers become laminated to each other effectively in situ when they are heated to an elevated temperature and placed in a pressurized hydrogen-bearing feed stream fed to the cell or module. Alternatively, the coating and flexible layers are first laminated together by depositing the coating layer onto the flexible intermediate layer by electroless or electrolytic plating, chemical vapor deposition, plasma deposition, sputtering or thermal evaporation or spraying methods, followed by placing the so-laminated coating/flexible layer in contact with the base metal layer and securing the composite into a test cell or module as noted above.

When a textured coating metal layer is used, texturing may be induced in that layer either during lamination of the coating metal layer to the support layer during operation of the module or as a separate step, or prior to assembly of the composite membrane, for example, by stamping or pressing a texturing pattern into the layer.

Figure 1B:
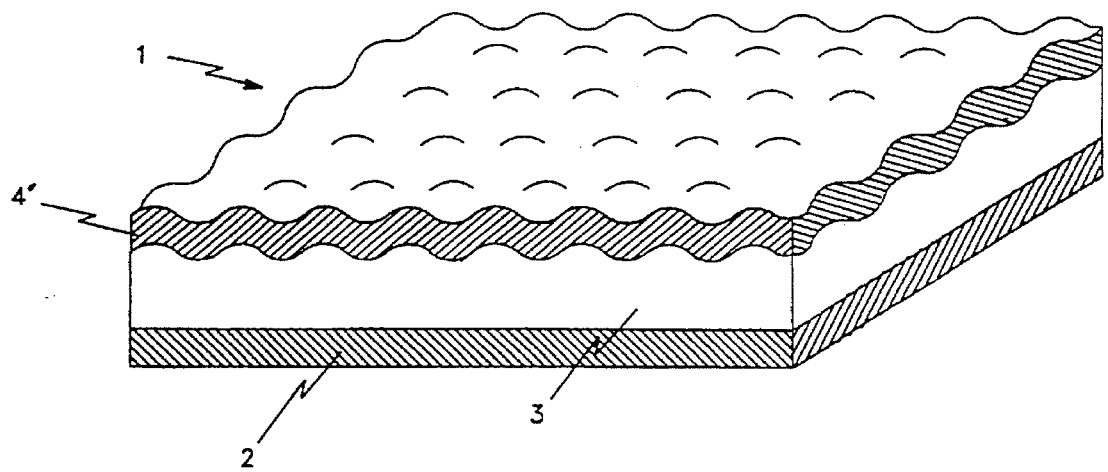

FIG. 1b shows a preferred embodiment of a three-layer composite membrane 1 comprising a support matrix 2, a flexible, non-sintered, porous or microporous intermediate layer 3, and a textured coating metal layer 4' (which may comprise one or more layers). Such an ordered arrangement of the texturing as shown in FIG. 1b is not essential, and the texturing may be randomly distributed over the coating metal layer. In use, the composite hydrogen separation membrane of the present invention is typically incorporated into a module.

A preferred annular geometry for the hydrogen separation element 20 is shown in FIGS. 2a–2d. Central hole 21 provides for collection of permeated hydrogen. A peripheral hollow 23 is provided, which may be a notch, a slot, a series of notches or slots, or a truncated section at the perimeter of the separation membrane. Such peripheral hollows provide a pathway for the flow of the feed stream to successive separation elements if multiple elements are used in a module.

Figure 3A:
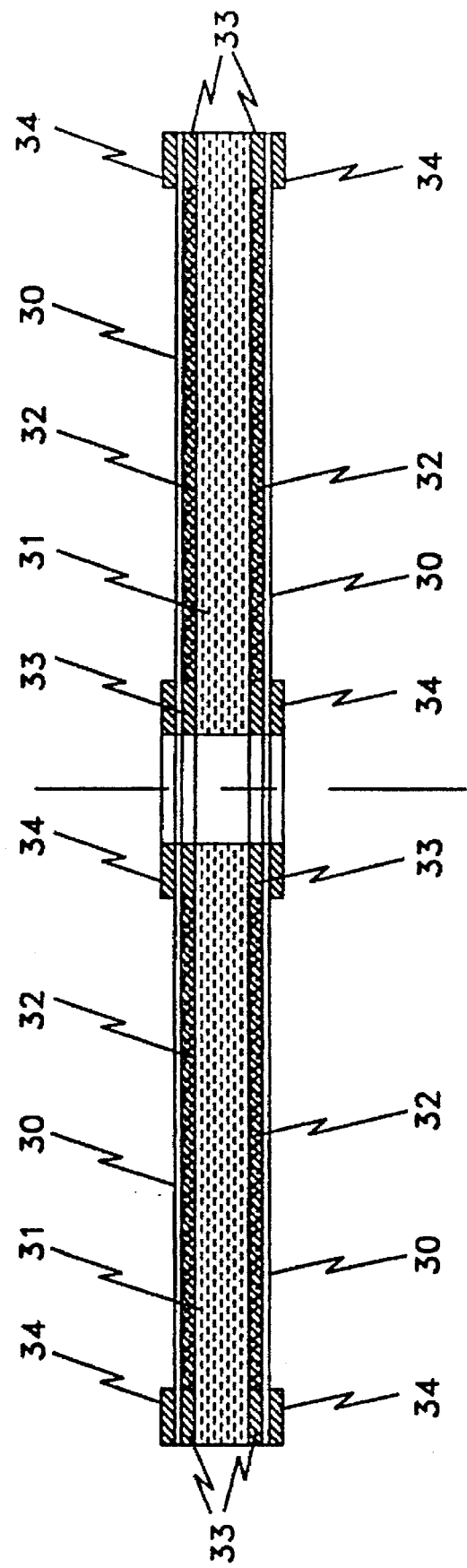
FIGS. 3a and 3b are schematic cross-sectional views of exemplary separation membrane pairs of the present invention.
Figure 3B:
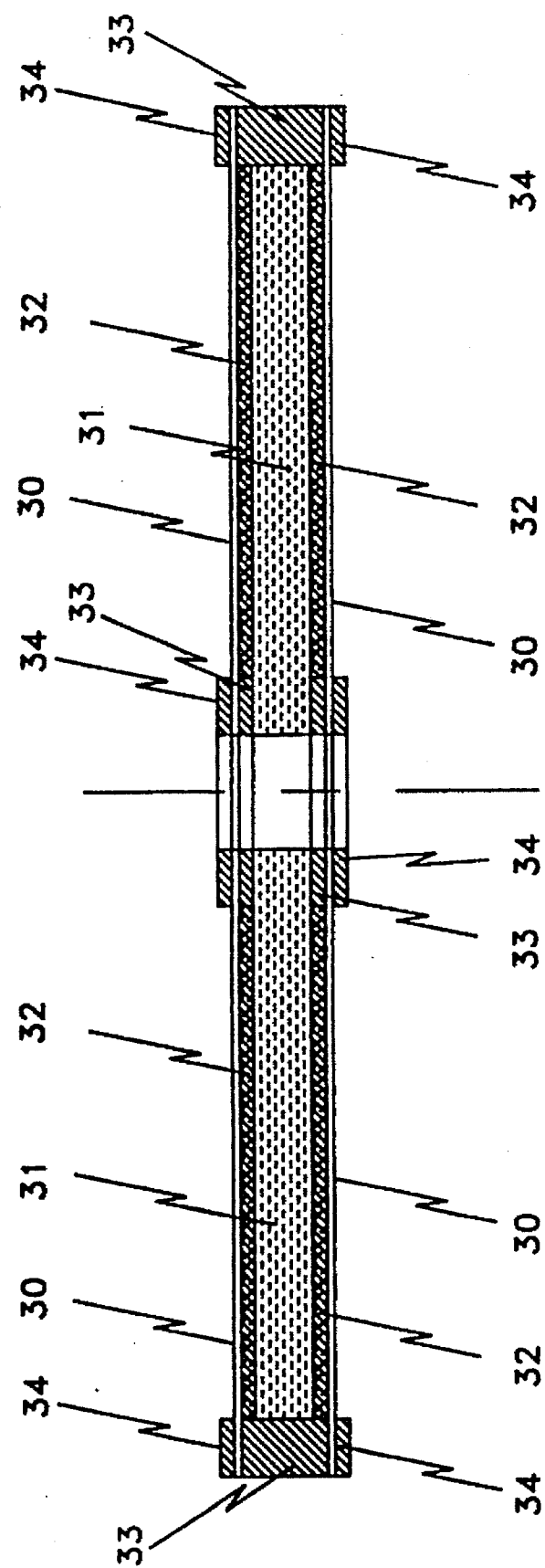

Separation element 20 consists of two annular hydrogen separation membranes placed on either side of an annular support matrix as shown in FIGS. 3a and 3b. For each separation element 20, coating metal layer 30 is separated from the support matrix 31 by the intermediate layer 32. Annular metal spacers 33, preferably of copper, nickel, iron, silver, gold, palladium, platinum or alloys of these metals, are located at the peripheries of both separation element 20 and central hole 21. In FIG. 3b, metal spacer 33 forms a band around the perimeter of support matrix 31. A gas-tight seal, such as welding, brazing, or diffusion bonding, is used to seal coating metal layer 30 of the hydrogen separation membrane to metal spacers 33, and to seal metal spacers 33 to support matrix 31. An optional overlayment 34, also preferably of copper, iron, nickel, silver, gold, palladium, platinum or alloys of these metals, may be placed over the surface of coating metal layer 30 at central hole 21 and around the perimeter of the entire assembly to reduce the risk of damage to coating metal layer 30 during fabrication of the separation element.

Figure 2:
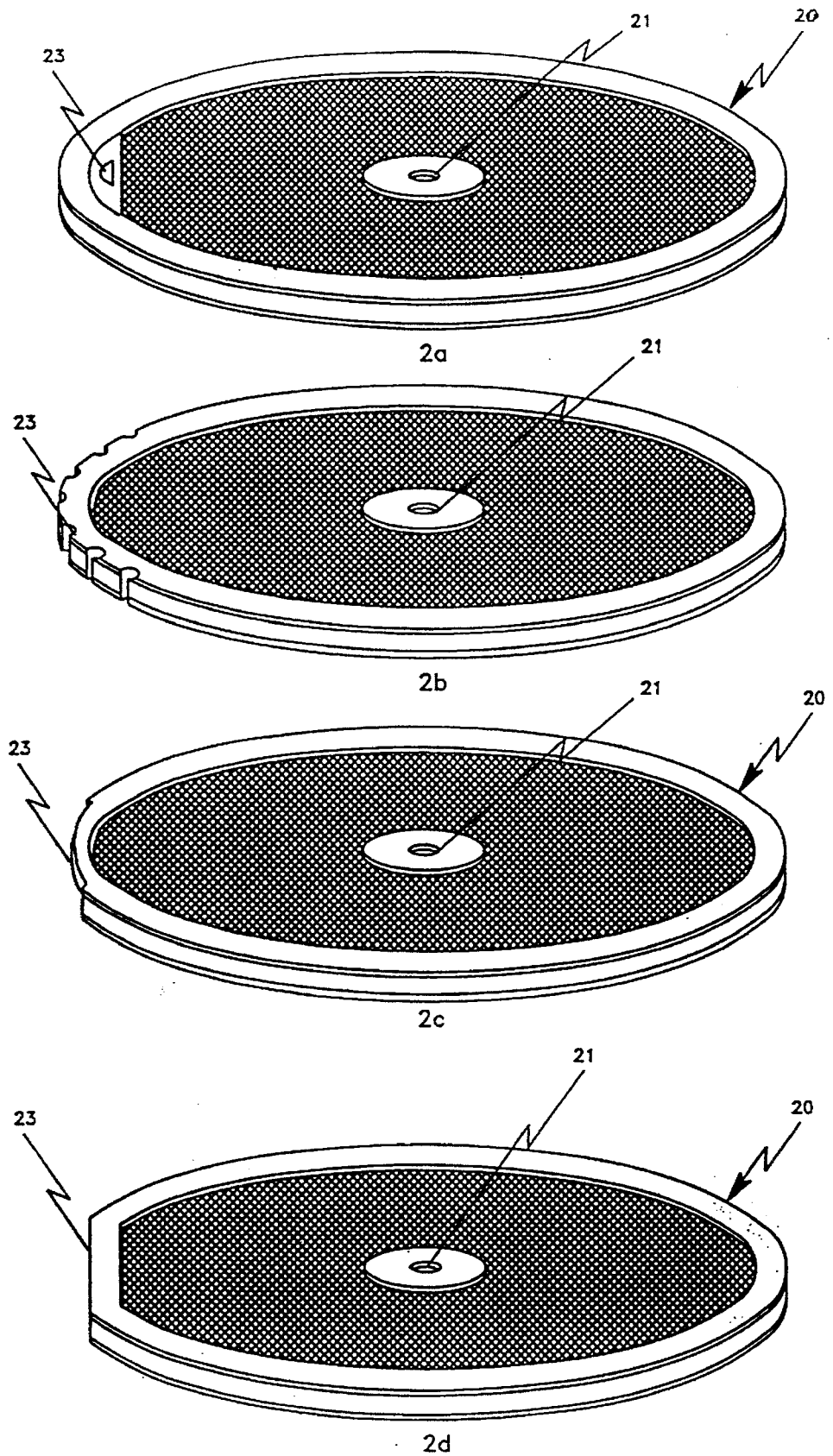
FIGS. 2a–2d are representations of pairs of composite separation membrane of the present invention showing various designs for providing a pathway for the feed stream to flow to successive separation membrane pairs in a module.
Figure 4:
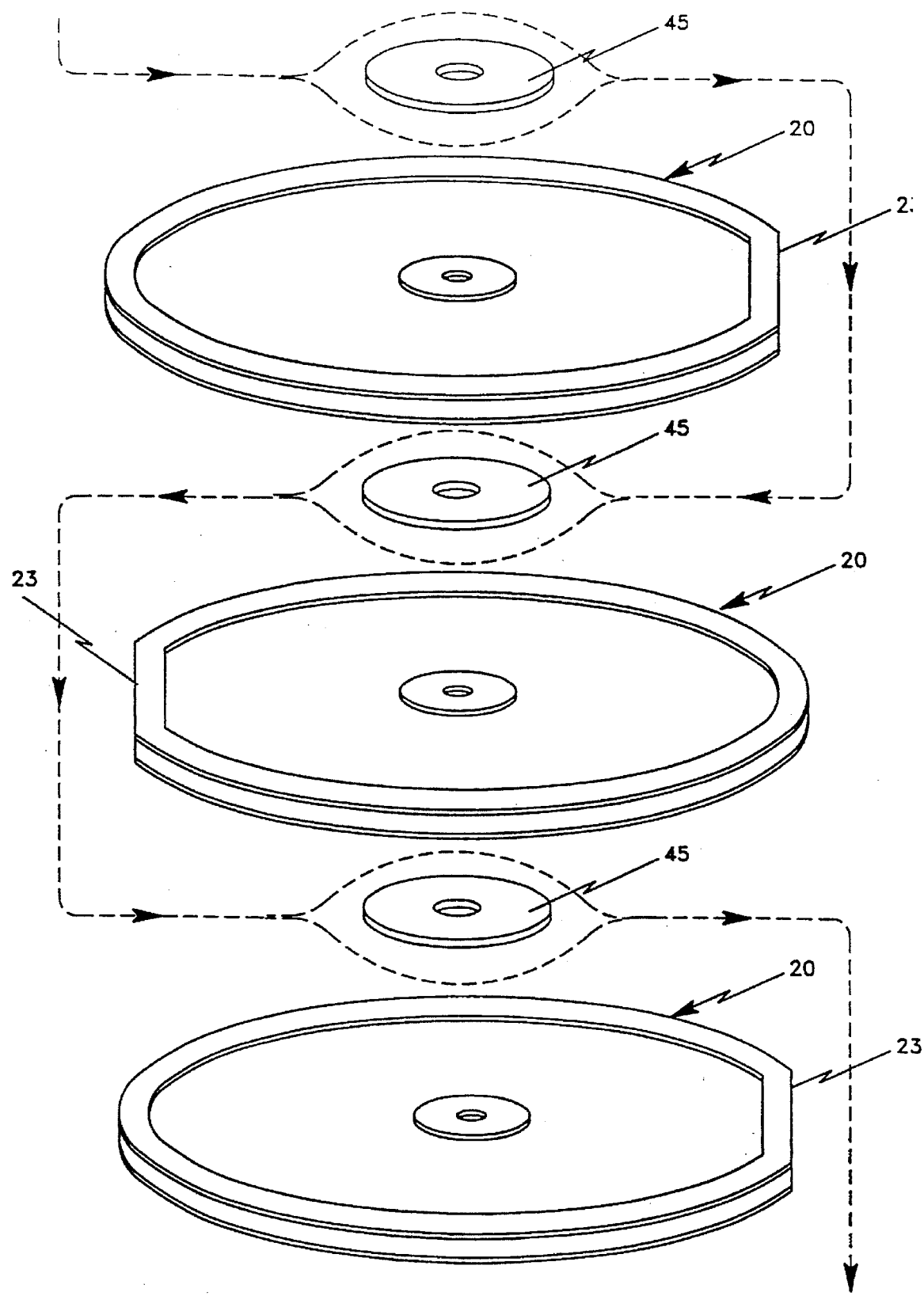
FIG. 4 shows a pathway for the feed stream to flow over a representative stack in an exploded view of three separation membrane pairs.

Multiple separation elements 20 may be stacked to increase the total membrane surface area, for example as shown in FIG. 4. The feed stream containing hydrogen flows over the outer surfaces of separation elements 20 and around gaskets 45 as shown by the dashed line in the drawing. As shown in FIG. 4, the peripheral hollow 23 in each separation element is oriented approximately 180° in relation to the hollow in adjacent separation elements. As shown in FIG. 2b and 2c, a series of notches or a slot at the perimeter of the separation element may be employed in place of a single notch (FIG. 2d) without altering the orientation of the separation elements or significantly altering the feed flow pathway (shown in FIG. 4). The orientation of the peripheral hollow in one separation element with respect to the hollow in an adjacent separation element is determined so as to maximize the surface area of the separation element contacted by feed stream gases. This orientation is preferably, but not necessarily, 180° out of phase with adjacent elements.

Figure 5:
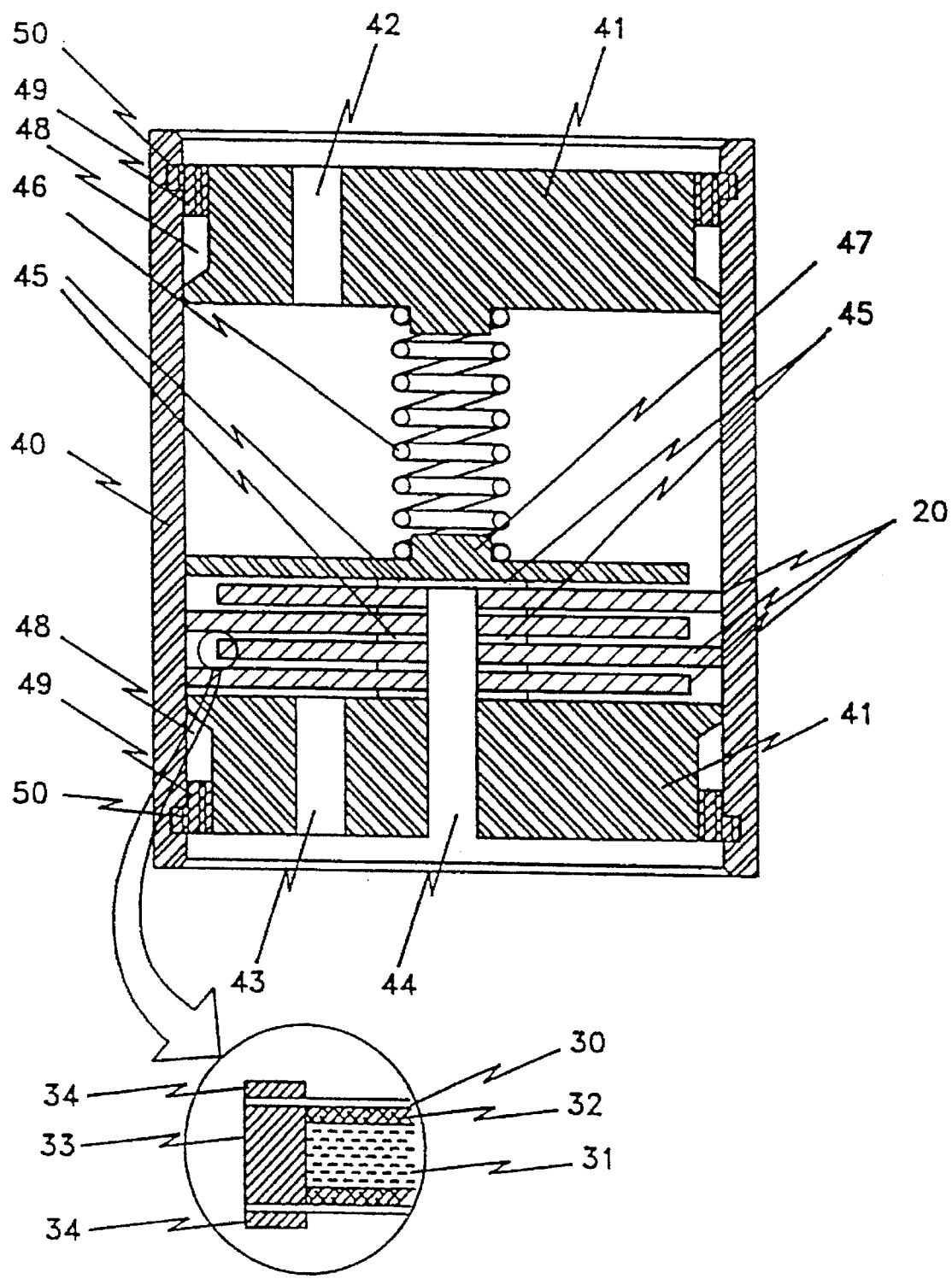
FIG. 5 is a cross-sectional view of a cylindrical module containing a stack of four separation membrane pairs and utilizing a gas-tight shell to confine the feed gas within the module.

A stack of separation elements 20 may be placed in a shell 40 to make up a membrane module, as shown in FIG. 5. The module is equipped with two end plates 41, at least one feed inlet port 42, at least one permeate outlet port 44, and at least one raffinate (hydrogen-depleted feed) discharge port 43. One endplate 41 may be welded to the shell 40. During operation of the module hydrogen permeates the coating metal layer of the hydrogen separation membrane and is collected in the voids within the support matrix. Permeate hydrogen then flows to central hole 21 of annular separation element 20 and exits the module through at least one permeate outlet port 44 as the permeate stream containing product hydrogen. Gaskets 45 provide a gas-tight seal between successive separation elements 20 in the stack to prevent cross-contamination between the feed stream and the permeate stream. Gaskets 45 may be graphite (e.g., Grafoil™, made by Union Carbide Corp.); a soft metal (e.g., copper, nickel, iron, silver, gold, palladium, platinum, and alloys of these metals); asbestos or other metal oxide, or a composite of these three, such as graphite/metal or asbestos/metal. Brazing, soldering, welding, or diffusion bonding may also be used to achieve a gas-tight seal between successive separation elements, but the use of gaskets offers several advantages, including ease of module fabrication and ease of membrane replacement.

Still referring to FIG. 5, the stack of separation elements 20 is maintained under a compressive loading by means of spring 46 such that the gaskets 45 are kept under loading to ensure that a gas-tight seal is maintained during operation. Spring 46 bears against separation elements 20 by way of load-bearing plate 47. Alternative means (not illustrated) for achieving compressive loading on separation elements 20 include a set screw through one end plate 41 to compress the element stack against the opposite end plate; a compression rod or tube that would compress the separation element stack against one end plate by running through the central permeate holes 21 of the separation element stack that have a smaller diameter so as to provide a sufficient annular space between the outer diameter of the compression rod and the diameter of the central permeate hole 21 to provide sufficient permeate hydrogen flow with minimal pressure drop. Permeate hydrogen flow is also possible with the use of a grooved or splined rod, or by using a tubular rod that is perforated or slotted to allow permeate hydrogen to pass through the wall of the tube and out of the module through its center while retaining sufficient mechanical strength to compress the membrane element stack under the anticipated operating conditions. End plates 41 are sealed to the module shell 40 by end plate gasket 48, which is preferably a high-temperature gasket material such as Grafoil™. Slip ring 49 bears against end-plate gasket 48. Slip ring 49 and end plate 41 are secured with locking ring 50.

Figure 6:
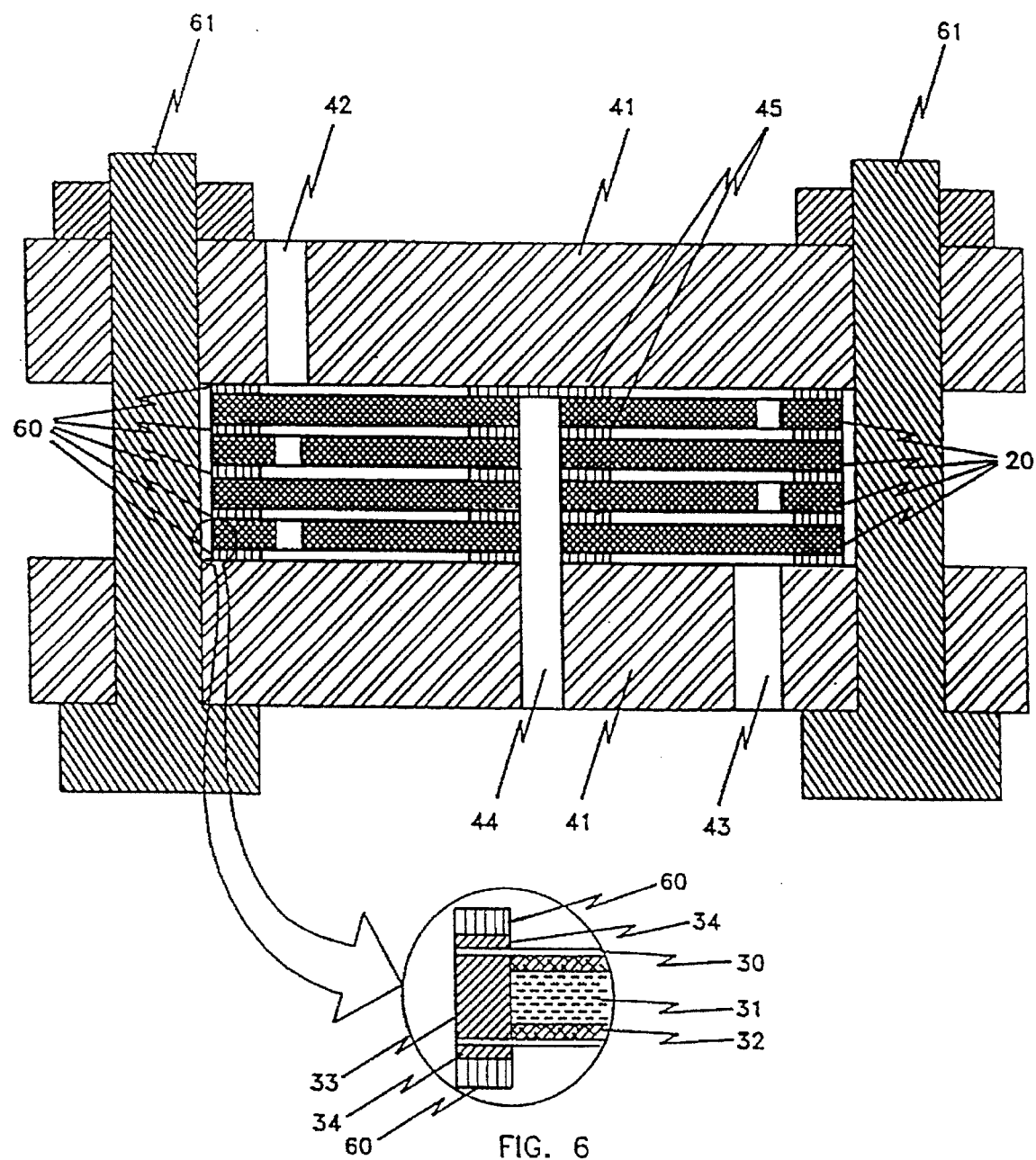
FIG. 6 is a cross-sectional view of another cylindrical module containing a stack of four separation membrane pairs and utilizing perimeter gaskets to confine the feed gas within the module.

FIG. 6 shows an alternative module configuration in which perimeter gaskets 60 are utilized between membrane separation elements 20. Use of perimeter gaskets 60 eliminates the need for a gas-tight shell 40 to confine the feed gas within the module. In this module configuration the membrane separation elements 20 are of the design depicted in FIG. 2a. An advantage of using perimeter gaskets 60 to assemble the membrane module is that any leaks through the edges of membrane separation elements 20 are to the exterior of the module, eliminating the potential for the leak to contaminate permeate hydrogen by the feed stream.

Still referring to FIG. 6 the module is fitted with two end plates 41, at least one feed inlet port 42, at least one permeate outlet port 44, and at least one raffinate discharge port 43. End plates 41 are secured using bolts 61 or other mechanical fastening means. Gas flow during operation of the module shown in FIG. 6 is the same as described above in connection with FIG. 5. Gasket 45 provides a gas-tight seal between successive separation elements 20 in the stack to prevent cross contamination between the feed and permeate streams. Gaskets 45 and 60 may be of the same materials mentioned in connection with the embodiment described in FIG. 5, and brazing, soldering, welding, or diffusion bonding may also be used to achieve the gas-tight seal between successive separation elements.

Figure 7A:
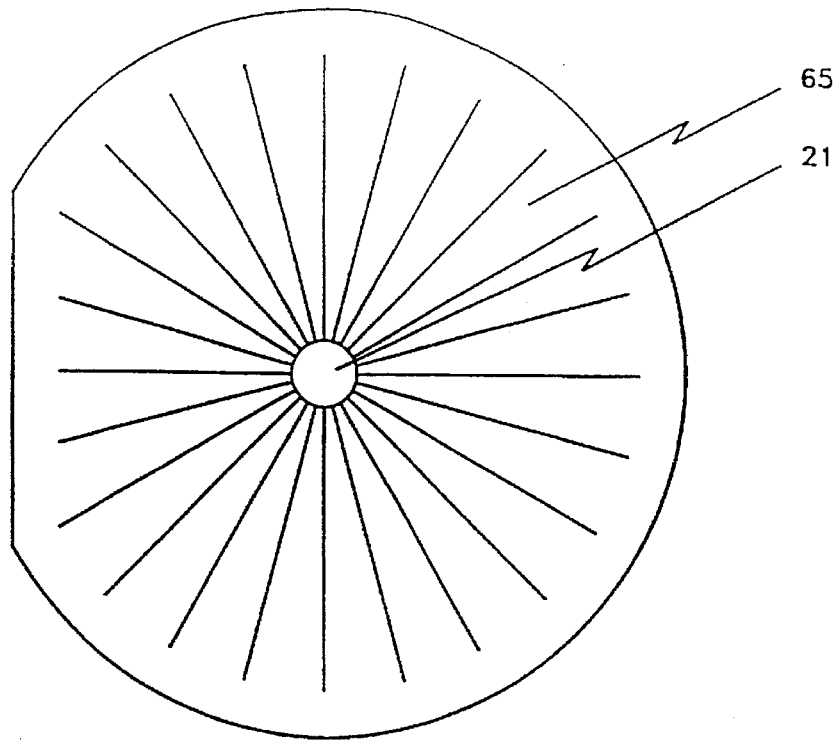
FIG. 7a is a top view of an exemplary support matrix showing slots to facilitate flow of the permeate hydrogen to the common-axis hole of the composite separation membrane.
Figure 7B:
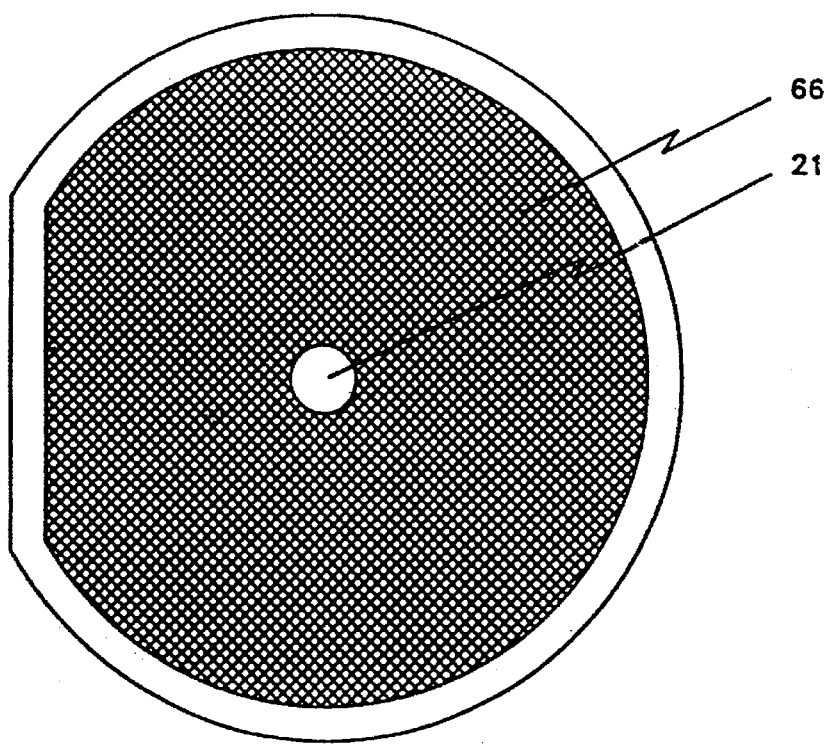
FIG. 7b is a plan view of the support matrix showing a wire mesh insert to facilitate flow of the permeate hydrogen to the common-axis hole of the composite separation membrane.

The support matrix provides mechanical strength to the separation element. Preferred materials for the support matrix include stainless steel and carbon sheet steel, perforated and non-perforated; metal wire mesh; and porous sintered metal sheet. An especially preferred material for the support matrix is a slotted steel plate as shown in FIG. 7a. The slots 65 are arranged radially and provide conduits for the flow of permeate hydrogen to central hole 21 in the support matrix. Alternatively, the support matrix may be a porous metal such as steel (not shown), or a metal mesh 66, as shown in FIG. 7b.

In the foregoing exemplary embodiments of the invention, the module has circular symmetry through its cross-section. Other cross-sectional geometries are also suitable, such as square, rectangular, and triangular. However, circular cross-sectional symmetry leads to significantly reduced fabrication costs, and so, this geometry is especially preferred.

The membrane modules incorporating the hydrogen separation elements are preferably operated at a temperature between 200° C. and 1000° C., with an especially preferred operating temperature range of 300° C. to 500° C. The module may be externally heated to the operating temperature, or it may be heated by flowing the feed gas through a preheater, the hot feed gas serving to maintain the module at the operating temperature. If the feed gas, as produced, is hotter than the desired operating temperature of the module it may be possible to use the hot feed gas directly to heat the module to the operating temperature without any additional input of energy.

Figure 8:
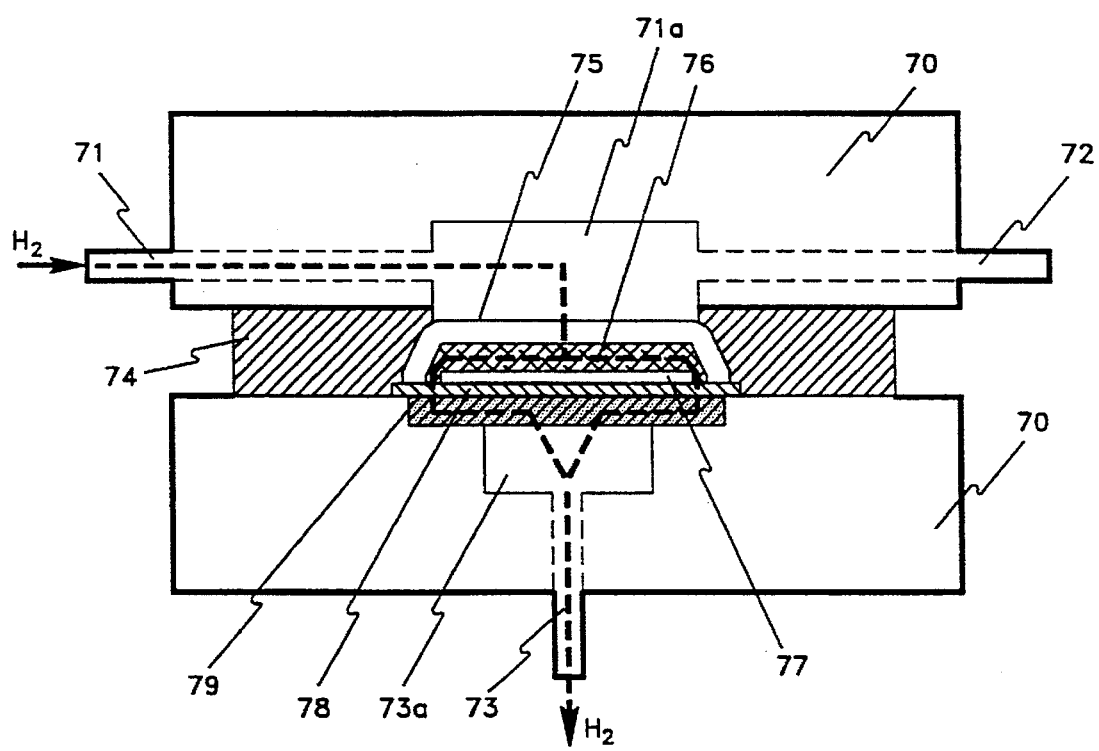
FIG. 8 is a cross-sectional view of a permeation test cell used to measure the performance of composite membranes of the present invention.

FIG. 8 is a cross-sectional view of a permeation test cell 70 showing the placement of a composite membrane of the present invention in the test cell. The two halves of the cell 70 are fitted with a feed inlet port 71, a feed plenum 71a, a raffinate port 72, a permeate plenum 73a and a permeate port 73. A grafoil gasket 74 seals the Composite membrane into the cell, and seals to the surface of the Pd coating metal layer 75. A fabric intermediate layer 76 is placed between the Pd layer and a stainless steel support matrix 77. Combined layers 75, 76 and 77 form the composite metal membrane. To prevent intermetallic diffusion between the test cell 70 and the support matrix 77, and thus to permit reuse of the test cell, an aluminum oxide disc 78 is placed between the support matrix 77 and a sintered steel disc 79 which is part of the permeate half of the cell and also serves as a support element. The steel disc 79 serves to collect the permeate hydrogen as shown by the dotted line hydrogen pathway. This type of permeation cell was useful in demonstrating the functional properties of composite membrane that are the subject of this invention.

EXAMPLE 1

A three-layer Pd/NEXTEL™ fabric/316 stainless steel composite membrane was prepared and tested for hydrogen permeability in a test cell having the construction shown in FIG. 8. The composite membrane, about 3 cm in diameter, comprised a Pd coating layer 75, 25 μm thick and a dense (i.e., nonporous and nonperforated) support matrix 77 of type 316 stainless steel 50 μm thick separated by a continuous layer 76 of NEXTEL™ (an aluminum oxide/silicon oxide/boron oxide flexible woven fabric). The composite membrane was fabricated by layering Pd foil on the NEXTEL fabric, followed by placement of those two layers on the stainless steel foil. The composite membrane was then mounted in a steel permeation cell 70 of the configuration shown in FIG. 8, using a graphite gasket 74 to achieve a gas-tight seal to the membrane, effectively isolating the feed chamber of the cell from the permeate chamber of the cell so that only hydrogen diffusing through the membrane from the feed stream could enter the permeate stream. A sintered steel disc 79 at the permeate side of the composite membrane was used to collect the permeate hydrogen. Because the test cell was made of steel, in order to prevent fusion between the steel cell and the stainless steel support of the composite membrane and so be able to reuse the test cell, a thin, porous aluminum oxide filtration disc 78 (ANODISC™ from Whatman Scientific of Maidstone, England) was placed between the stainless steel support matrix 77 of the composite membrane and the test cell 70. The three layers of the composite membrane were laminated in situ by the operating temperature (400° C.) of the cell and the pressure (100 psig) of the feed stream. The composite membrane was tested for hydrogen permeability by measuring the flow rate of the permeate stream. As shown in FIG. 8, hydrogen gas is fed through feed inlet port 71 to feed plenum 71a, wherein it contacts and diffuses through the Pd coating metal layer 75, then hydrogen gas diffuses through fabric intermediate layer 76 and around support matrix 77, then through the ANODISC™ diffusion barrier disc 78, sintered steel disc 79, permeate plenum 73a and permeate outlet port 73.

The average hydrogen flux through the composite membrane was measured at 400° C. using a 99.95% pure hydrogen gas feed stream at 100 psig (780 kPa), the permeated hydrogen being at ambient pressure. The average hydrogen flux was 79 std ft$^3$/ft$^2$·hr (24 m$^3$/m$^2$·hr).

EXAMPLE 2

Substantially the same composite membrane of Example 1 was tested for hydrogen permeability at 400° C. over an extended period of time. The average initial flux was 75 std ft$^3$/ft$^2$·hr (23 m$^3$/m$^2$·hr) and after 30 days' continuous operation at 400° C., the average hydrogen flux through the membrane was still the same.

EXAMPLE 3

Substantially the same composite membrane of Example 1, with the exception that the support matrix was nickel about 30 μm thick, was tested for hydrogen permeation. Average flux through this membrane was 71 std ft$^3$/ft$^2$·hr (22 m$^3$/m$^2$·hr).

EXAMPLE 3

Substantially the same composite membrane of Example 1, with the exception that the support matrix was copper about 30 μm thick, was tested for hydrogen permeation. Average flux through this membrane at 400° C. was 62 std ft$^3$/ft$^2$·hr (19 m$^3$/m$^2$·hr).

EXAMPLE 5

Substantially the same composite membrane of Example 1, with the exception that the intermediate layer was SILTEMP 84CH (a silicon oxide fabric) about 350 μm thick, coated with an aluminum oxide slurry, was fabricated as in Example 1 with the exceptions noted herein. The aluminum oxide slurry was prepared by coating one side of the silicon oxide fabric with a suspension of aluminum oxide (DISPERAL™ by Condea of Germany) in methanol (1 g aluminum oxide in 2.5 mL methanol). Glycerol (0.5 g) was added to the suspension as a stabilizer to help keep the aluminum oxide particles suspended. The so-coated silicon oxide fabric was then dried in air and then heated to 700° C. in air to remove the organic residue from the aluminum oxide slurry coating. The aluminum oxide slurry coating, applied in this manner, filled the large voids in the silicon oxide textile and yielded a smooth, but porous, non-sintered surface.

The average flux through this membrane was measured at 600° C. over an extended period and initially was found to be 153 std ft$^3$/ft$^2$·hr (47 m$^3$/m$^2$·hr), and the same after 15 days' operation.

EXAMPLE 6

Substantially the same composite membrane of Example 1, with the exception that the coating metal layer was silicon oxide-coated palladium about 25 μm thick, was tested for hydrogen permeation. The silicon oxide coating was microporous and was only on the surface of the palladium facing the feed stream, and was deposited on the palladium by plasma deposition. The thickness of the silicon oxide coating varied from about 0.1 to 1 μm. Average flux through this membrane at 400° C. was 30 std ft$^3$/ft$^2$·hr (9.1 m$^3$/m$^2$·hr).

EXAMPLE 7

Substantially the same composite membrane of Example 1 was made, with the exception that the intermediate layer was a silicon oxide-based woven fabric (SILTEMP™ 84CH, from Ametek, Inc.) about 350 μm thick, and was tested for hydrogen permeation. Average flux through this membrane at 400° C. was 70 std ft$^3$/ft$^2$·hr (21 m$^3$/m$^2$·hr).

EXAMPLE 8

Substantially the same composite membrane of Example 7 was prepared, with the exception that the support matrix layer was perforated stainless steel about 210 μm thick having a straight pattern of holes about 825 μm in diameter, rendering about 30% of the surface perforated. The membrane was tested for hydrogen permeation and exhibited an average flux of 70 std ft$^3$/ft$^2$·hr (21 m$^3$/m$^2$·hr) at 400° C.

EXAMPLE 9

Substantially the same composite membrane of Example 1 was made, with the exception that the intermediate layer was fiberglass cloth (from McMaster-Carr Supply Co. of Los Angeles, Calif.) about 300 μm thick, and was tested for hydrogen permeation. Average flux through this membrane at 400° C. was 45 std ft$^3$/ft$^2$·hr (14 m$^3$/m$^2$·hr).

EXAMPLE 10

Substantially the same composite membrane of Example 9 was made, with the exception that the support matrix layer was perforated stainless steel of the type described in Example 8, and was tested for hydrogen permeation. Average flux through this membrane at 400° C. was 90 std ft$^3$/ft$^2$·hr (27 m$^3$/m$^2$·hr).

EXAMPLE 11

Substantially the same composite membrane of Example 9 was made, with the exception that the coating metal layer was an alloy of palladium with 5% iridium about 25 μm thick, and was tested for hydrogen permeation. Average flux through this membrane at 600° C. was 110 std ft$^3$/ft$^2$·hr (34 m$^3$/m$^2$·hr).

EXAMPLE 12

Substantially the same composite membrane of Example 9 was made, with the exception that the coating metal layer was a Pd-25Ag alloy about 25 μm thick, and was tested for hydrogen permeation. Average flux through this membrane at 400° C. was 145 std ft$^3$/ft$^2$·hr (44 m$^3$/m$^2$·hr) and at 600° C. was 206 std ft$^3$/ft$^2$·hr (63 m$^3$/m$^2$·hr).

EXAMPLE 13

Substantially the same composite membrane of Example 1 was made, with the exception that the intermediate layer was aluminum oxide paper (type APA-3 from Zircar Products, Inc.) about 330 μm thick. Prior to fabricating the composite metal membrane, the aluminum oxide paper was calcined in air at 800° C. to remove organic binders. Average hydrogen flux through this membrane at 400° C. was 76 std ft$^3$/ft$^2$·hr (23 m$^3$/m$^2$·hr).

EXAMPLE 14

Substantially the same composite membrane of Example 13 was made, with the exception that the intermediate layer was aluminum oxide felt (type APA-2 from Zircar Products) about 1000 μm thick as received and without compressing the fibers, and was tested for hydrogen permeation. Average flux through this membrane at 400° C. was 77 std ft$^3$/ft$^2$·hr (23 m$^3$/m$^2$·hr).

Comparative Example

To illustrate the problems associated with the use of a sintered rigid ceramic support instead of flexible fabric as the intermediate layer in the composite metal membrane, a composite membrane was made by laminating a palladium-nickel (nominally 25% palladium and 75% nickel) coating metal layer about 20 μm thick over a rigid porous aluminum oxide intermediate layer (ANODISC™ from Whatman Scientific of Maidstone, England) having a much smaller coefficient of thermal expansion than the stainless steel used to fabricate the permeation cell. The combined palladium-nickel/aluminum oxide layers were placed on a support matrix of sintered stainless steel and tested for hydrogen permeability at 500° C. as described in Example 1. However, due to an excessively high hydrogen flow rate, no initial flux measurement could be made. A leak test was conducted using argon at 100 psig (780 kPa). The argon flow rate through the permeate line was also too high to measure, indicating a large leak from the feed stream to the permeate stream.

Upon cooling and dismantling the permeation cell, the membrane was found to be broken into many pieces. The aluminum oxide intermediate layer was observed to be fractured, apparently causing the fracture of the palladium-nickel coating metal.

EXAMPLE 15

A membrane module of substantially the same design as depicted in FIG. 5 and containing four membrane separation elements was fabricated in the following manner. The shell 40, end plates 41, and load-bearing plate 47 were machined from type 304 stainless steel. Spring 46 was a stack of seven disc springs placed in series (Schnorr Corporation, Woodside, N.Y.; part number 015000, outside diameter 56 mm, thickness 2 mm, with a central hole 28.5 mm diameter). This spring provided a compressive load of 8300 psig (585 kg/cm$^2$) on the stack of membrane separation elements 20. Graphite/metal composite spiral-wound gaskets 45 (Flexitallic Company, Deerpark, Tex.) were used to achieve a gas-tight seal and a 0.13 cm spacing between separation elements 20. The gap between separation elements 20 and the interior of the shell was about 0.04 cm.

The membrane separation elements, each about 0.36 cm thick, were of the design shown in FIG. 3b. The coating metal layer 30 was a foil nominally 28 μm thick and composed of an alloy containing about 40 wt % Cu and 60 wt % Pd. The intermediate layer 32 was composed of SILTEMP™84CH fabric. Prior to use, the SILTEMP™ 84CH fabric was heated in air to 400° C. to remove organic sizing agents, then cooled to room temperature, then coated with Alumina Rigidizer/Hardener (Zircar Products, Inc., Florida, New York) to stiffen the fabric and improve its handling qualities; then heated again in air to 400° C. for 4 hours to 18 hours to remove the organic dye introduced with the Rigidizer/Hardener. Support matrix 31 was a slotted stainless steel plate of the type shown in FIG. 7a. Spacers 33 of Cu were placed around the perimeter of central hole 21 and around the perimeter of the support matrix, the latter procedure forming a tight-fitting band around the outer edge of the support matrix. Spacer band 33 projected 0.05 cm above the surface of the support matrix to provide a recess for the intermediate layer as shown in FIG. 3b. Spacer band 33 was affixed to the support matrix by a frictional fit.

Overlayment 34 was composed of Cu and was 0.025 cm thick. The components of the separation element were assembled as shown in FIG. 3b. To achieve the necessary bond between spacers 33, coating metal layer 30, and overlayments 34, the entire assembly was placed between rigid plates and heated to 500° C. for 2 hours under one atmosphere of hydrogen, to cause diffusion bonding between the elements, resulting in a gas-tight seal.

The module was equipped with a feed inlet port 42 in one end plate and a raffinate discharge port 43 in the other end plate so that the feed stream could flow through a continuous path over the feed side surfaces of all four separation elements sequentially, and then exit the module. Product hydrogen was collected from each separation element into the permeate Outlet port 44.

After heating the module to 350° C., its operation was demonstrated by flowing 99.95% pure hydrogen into the feed side of the module at 100 psig (780 kPa), the permeate hydrogen exiting the module at ambient pressure. The average flux was 35 std ft$^3$/ft$^2$hr (10.6 m$^3$/m$^2$hr).

The terms and expressions employed in the foregoing specification are used therein as terms of description and not of limitation, and there is no intention in the use of such terms and expressions of excluding equivalents of the features shown and described or portions thereof, it being recognized that the scope of the invention is defined and limited only by the claims which follow.

What is claimed is:

1. A process for the separation of hydrogen from other gases comprising:

(a) providing a feed gas comprising a mixture of gases containing hydrogen;

(b) providing a hydrogen separation element which, after fabrication, comprises a nonporous hydrogen-permeable coating metal layer supported by a rigid ceramic, carbon, or metal support matrix, and a porous intermediate layer between said coating metal layer and said support matrix, wherein, at a temperature of from about 200° C. to about 1000° C., said intermediate layer does not chemically react with hydrogen or with said coating metal layer or with said support matrix to form a hydrogen-impermeable layer, and said support matrix does not react with hydrogen or with said intermeiate layer to substantially reduce the tensile strength of said support matrix, and wherein each of said coating metal layer, said support matrix and said inter mediate layer are planar and have at least one common axis hole therethrough in alignment along a common axis and having a gas-tight gasket about the periphery of said at least one hole of said coating metal layer;

(c) contacting said feed gas with said hydrogen separation element to form a hydrogen permeate stream; and (d) collecting said hydrogen permeate stream.

2. The process of claim 1 conducted at a temperature in the range of about 200° C. to about 700° C.

3. The process of claim 2 wherein the hydrogen partial pressure of said feed gas is at least one atmosphere.

4. The process of claim 3 wherein said feed gas includes at least one sulfur compound in a concentration of at least 10 ppmv, and said coating metal layer of said hydrogen separation element comprises a Pd-Cu alloy.

5. The process of claim 4 wherein said Pd-Cu alloy is 50–55 atom % Cu, balance Pd.

6. The process of claim 5 conducted at a temperature in the range from about 500° C. to about 800° C.

7. A hydrogen separation module comprising a housing that has at least one feed inlet, at least one permeate outlet, at least one raffinate outlet and at least one hydrogen separation element which, after fabrication, comprises a nonporous hydrogen-permeable coating metal layer supported by a rigid ceramic, carbon, or metal support matrix, and a porous intermediate layer between said coating metal layer and said support matrix, wherein, at a temperature of from about 200° C. to about 1000° C., said intermediate layer does not chemically react with hydrogen or with said coating metal layer or with said support matrix to form a hydrogen-impermeable layer, and said support matrix does not react with hydrogen or with said intermediate layer to substantially reduce the tensile strength of said support matrix, and wherein each of said coating metal layer, said support matrix and said intermediate layer are planar and have at least one common axis hole therethrough in alignment along a common axis and having a gas-tight gasket about the periphery of said at least one hole of said coating metal layer.

8. The module of claim 7 wherein said coating metal layer, said support matrix and said intermediate layer have a common regular geometric shape.

9. The module of claim 8 wherein said coating metal layer, said support matrix, and said intermediate layer are annular in shape.

10. The module of claim 8 or 9, including a first hydrogen-impermeable spacer about the periphery of said intermediate layer and between said coating metal layer and said support matrix, and a second hydrogen-impermeable spacer associated with said at least one hole and located between said coating metal layer and said support matrix.

11. The module of claim 10 wherein said first and second spacers are integral with said support matrix.

12. The module of claim 10 wherein said first and second spacers are separate elements bonded to said support matrix.

13. The module of claim 10 wherein said first and second spacers are formed of a metal selected from Cu, Ni, Fe, Al and alloys thereof.

14. The module of claims 7 or 8 or 9 wherein said coating metal layer is textured.

15. The module of claims 7 or 8 or 9 wherein said coating metal layer is a hydrogen-permeable metal selected from a transition metal, alloys and composites thereof, said coating metal layer being chemically and physically stable at temperatures of at least 200° C.

16. The module of claim 15 wherein said coating metal layer is selected from the group consisting of the transition metals from Groups VIIB and VIIIB of the Periodic Table, and alloys containing $\geq 20$ wt % of said metals.

17. The module of claim 16 wherein said coating metal layer is selected from the group consisting of Fe, Mn, Ni, Pd, Pt and Ru.

18. The module of claim 16 wherein said coating metal layer is an alloy selected from the group consisting of Pd-Ag, Pd-Cu and Pd-Ag-Cu.

19. The module of claim 18 wherein said alloy is a Pd-Ag alloy containing about 25 wt % Ag.

20. The module of claim 18 wherein said alloy is a Pd-Cu alloy containing about 40 wt % Cu.

21. The module of claims 7 or 8 or 9 wherein said intermediate layer is flexible.

22. The module of claim 21 wherein said intermediate layer is non-sintered.

23. The module of claims 7 or 8 or 9 wherein said intermediate layer is non-metallic.

24. The module of claims 7 or 8 or 9 wherein said intermediate layer is a fabric.

25. The module of claim 24 wherein said fabric is selected from woven and non-woven.

26. The module of claim 25 wherein said fabric is selected from a paper and a felt.

27. The module of claim 26 wherein said paper or felt is predominantly composed of fibers of a material selected from silicon dioxide, aluminum oxide, zirconium oxide, titanium oxide, yttrium oxide, hafnium oxide, vanadium oxide, niobium oxide, tantalum oxide, silicate glasses, borate glasses, carbon, and mixtures thereof.

28. The module of claim 25 wherein said intermediate layer is a woven fabric comprising woven fibers of a material selected from aluminum oxide, silicon oxide, mixtures containing $\geq 50\%$ aluminum oxide and silicon oxide, zirconium oxide, titanium oxide, yttrium oxide, hafnium oxide, vanadium oxide, niobium oxide, tantalum oxide, silicate glasses, borate glasses, carbon, and mixtures thereof.

29. The module of claim 25 wherein said intermediate layer is a non-woven fabric comprising non-woven fibers of a material selected from aluminum oxide, silicon oxide, mixtures containing $\geq 50\%$ aluminum oxide and silicon oxide, zirconium oxide, titanium oxide, yttrium oxide, hafnium oxide, vanadium oxide, niobium oxide, tantalum oxide, silicate glasses, borate glasses, carbon, and mixtures thereof.

30. The module of claims 7 or 8 or 9 wherein said intermediate layer comprises a material selected from aluminum oxide, silicon oxide, mixtures containing $\geq 50\%$ aluminum oxide and silicon oxide, zirconium oxide, titanium oxide, yttrium oxide, hafnium oxide, vanadium oxide, niobium oxide, tantalum oxide, silicate glasses, borate glasses, carbon, and mixtures thereof.

31. The module of claims 7 or 8 or 9 wherein said intermediate layer comprises a material selected from a metal oxide, a metal carbide, a metal nitride, a metal sulfide, and mixtures thereof.

32. The module of claims 7 or 8 or 9 wherein said support matrix is a material selected from ceramic, metal, carbon and mixtures thereof.

33. The module of claims 7 or 8 or 9 wherein said support matrix is metal and is in a form selected from a perforated sheet, a non-perforated sheet, a slotted sheet, a mesh, a porous sheet and a nonporous sheet.

34. The module of claims 7 or 8 of 9 wherein said intermediate layer is woven or textured and said coating metal is textured by pressing said coating metal in the form of a foil onto said intermediate layer.

35. The module of claim 7 or 8 or 9 wherein said housing comprises a multiplicity of said hydrogen separation elements.

36. The module of claim 7 wherein said at least one common axis hole of each of said coating metal layer, said support matrix, and said intermediate layer comprise a gas flow channel.

37. The module of claim 36 wherein said gas flow channel is a feed channel.

38. The module of claim 7 wherein said gas flow channel is a permeate channel.

39. The module of claim 7 wherein said coating metal layer and said support matrix have at least one common peripheral hollow on their respective peripheries, said at least one common hollow comprising a feed gas flow channel.

40. The module of claim 39 comprising more than one hydrogen separation element, each having at least one of said common peripheral hollows, wherein said common peripheral hollows on adjacent hydrogen separation elements are not in radial alignment.

41. The module of claim 40 wherein said common peripheral hollows on said adjacent hydrogen separation elements are at least 5° out of radial alignment.

42. The module of claim 7 wherein said hydrogen separation element comprises two coating metal layers and two intermediate layers oriented on opposite sides of said support matrix.

43. A hydrogen separation element which, after fabrication, comprises a nonporous hydrogen-permeable coating metal layer supported by a rigid ceramic, carbon, or metal support matrix, and a porous intermediate layer between said coating metal layer and said support matrix, wherein, at a temperature of from about 200° C. to about 1000° C.

said intermediate layer does not chemically react with hydrogen or with said coating metal layer or with said support matrix to form a hydrogen-impermeable layer, and said support matrix does not react with hydrogen or with said intermediate layer to substantially reduce the tensile strength of said support matrix,
and wherein each of said coating metal layer, said support matrix and said intermediate layer are planar and have at least one common axis hole therethrough in alignment along a common axis and having a gas-tight seal about the periphery of said at least one hole of said coating metal layer.

* * * * *